(12) United States Patent
Bacus (10) Patent No.: US 6,962,789 B2
(45) Date of Patent: Nov. 8, 2005

(54) METHOD FOR QUANTITATING A PROTEIN BY IMAGE ANALYSIS

(75) Inventor: Sarah S. Bacus, Hinsdale, IL (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 09/760,120

(22) Filed: Jan. 12, 2001

(65) Prior Publication Data

US 2001/0049114 A1 Dec. 6, 2001

Related U.S. Application Data (60) Provisional application No. 60/176,515, filed on Jan. 12, 2000, and provisional application No. 60/176,514, filed on Jan. 12, 2000.

(51) Int. Cl.[7] .................. G01N 33/53; G01N 33/574
(52) U.S. Cl. .................. 435/7.23; 435/1.1; 435/7.21; 435/7.23; 435/7.24; 435/7.92; 435/40.51; 435/40.52; 435/363; 435/373; 435/395; 435/284.1; 435/287.9; 436/63; 436/64; 436/544; 436/546; 436/10; 436/15; 436/56; 436/164; 436/166; 436/171; 436/172; 422/52; 422/55; 422/62; 422/73; 422/82.05; 422/82.07
(58) Field of Search .................. 435/6, 7.1, 7.21, 435/7.23, 7.9, 7.92, 363, 1.1, 7.2, 7.24, 40.5, 40.51, 40.52, 373, 383, 395, 284.1, 287.9, 288.4, 808; 436/63, 64, 813, 164, 171, 172, 544, 546, 10, 15, 56, 166; 422/52, 55, 62, 73, 82.05, 82.07

(56) References Cited

U.S. PATENT DOCUMENTS

| | | | |
|---|---|---|---|
| 5,008,185 A | 4/1991 | Bacus | |
| 5,086,476 A | 2/1992 | Bacus | |
| 5,109,429 A | 4/1992 | Bacus et al. | |
| 5,202,931 A | 4/1993 | Bacus | |
| 5,514,554 A | 5/1996 | Bacus | |
| 5,846,749 A | * 12/1998 | Slamon et al. | ............. 435/7.23 |
| 5,998,151 A | 12/1999 | Johnston et al. | |
| 6,007,996 A | * 12/1999 | McNamara et al. | ............ 436/6 |
| 6,165,734 A | 12/2000 | Garini et al. | |
| 6,463,438 B1 | * 10/2002 | Veltri et al. | .................. 707/15 |

FOREIGN PATENT DOCUMENTS

| | | |
|---|---|---|
| EP | 0378 383 | 7/1990 |
| WO | WO 93 03741 | 3/1993 |
| WO | WO 00/23799 A | 4/2000 |

OTHER PUBLICATIONS

Bacus et al., Archives of Pathology and Laboratory Medicine, vol. 114, No. 2, 1990, pp. 164–169.

Bacus et al., American Journal of Pathology, vol. 137, No. 1, Jul. 1990, pp. 103–111.

Van Diest et al., Analytical Cellular Pathology, vol. 3, No. 4, 1991, pp. 195–202.

Muss et al., 1994, N. Engl. J. Med. 330:1260–66.

Kraus et al., 1989, Proc. Natl. Acad. Sci. U.S.A. 86:9193–97.

(Continued)

*Primary Examiner*—Chris Chin
*Assistant Examiner*—Gailene R. Gabel
(74) *Attorney, Agent, or Firm*—McDonnell Boehnen Hulbert & Berghoff LLP (57) ABSTRACT

The present invention provides a method for determining expression levels of one or a multiplicity of target proteins in a tissue or cell sample.

18 Claims, 8 Drawing Sheets

OTHER PUBLICATIONS

Mendelsohn, 1990, Semin. Cancer Biol. 1:339–44.
Hancock et al., 1991, Cancer Res. 51:4575–80.
Peles et al., 1991, EMBO J. 10:2077–86.
Arteaga et al., 1994, Cancer Res., 54:3758–65.
Pietras et al., 1994, Oncogene 9:1829–38.
Cobleigh et al., 1999, J. Clin. Oncol. 17:2639–48.
Vincent et al., 2000, Cancer Chemother. Pharmacol. 45:231–38.
Lowry et al., 1951, J. Biol. Chem. 193:265–275.
Bacus et al., "Potential use of Image Analysis for the Evaluation of Cellular Predicting Factors for Therapeutic Response in Breast Cancers", Analytical and Quantitative Cytology and Histology, vol. 19 No. 4, Aug. 1997, pp. 316–328.
Bacus et al., "HER–2/neu oncogene expression, DNA ploidy and proliferation index in breast cancer", Analytical and Quantitative Cytology and Histology, vol. 14, No. 6, 1992 pp. 433–445.
Bacus et al., "HER–2/NEU Oncogene Expression and DNA Ploidy Analysis in Breast Cancer", American Journal of Pathology, vol. 114, No. 2, 1990, pp. 164–169.
Bacus et al., "HER–2/Neu oncogene expression and proliferation in breast cancer", American Journal of Pathology, vol. 137, No. 1—Jul. 1990.
Cobleigh et al., "Multinational Study of the Efficacy and Safety of Humanized Anti–HER2 Monoclonal Antibody in Women Who Have HER2–Overexpressing Metastatic Breast Cancer That Has Progressed After Chemotherapy for Metastatic Disease", 1999, J. Clin. Oncol. 17:2639–48.
Hancock et al., "A Monoclonal Antibody against the c–erbB–2 Protein Enhances the Cytotoxicity of cis–Dianninedichloroplatinum against Human Breast and Ovarian Tumor Cell Lines", 1991, Cancer Res. 51:4575–80.
Kraus et al., "Isolation and Characterization of ERBB3, a third member of the ERBB/epidermal growth factor receptor family: Evidence for overexpression in a subset of human mammary tumors", 1989, Proc. Natl. Acad. Sci. U.S.A. 86:9193–97.

Lowry et al., "Protein Measurement with the Folin Phenol Reagent", 1951, J. Biol. Chem. 193:265–275.

Mendelsohn, "The epidermal growth factor receptor as a target for therapy with antireceptor monoclonal antibodies" 1990, Semin. Cancer Biol. 1:339–44.

Muss et al., "c–erbB–2 Expression and Response to Adjuvant Therapy in Women with Node–Positive Early Breast Cancer", 1994, N. Engl. J. Med. 330:1260–66.

Peles et al., "Oncogenic Forms of the Neu/HER2 Tyrosine Kinase are Permanently Coupled to Phospholipase Cγ", 1991, EMBO J. 10:2077–86.

Peles et al., "Isolation of the Neu/HER–2 Stimulatory Ligand: A 44 kd Glycoprotein That Induces Differentiation of Mammary Tumor Cells", 1992, Cell 69:205–16.

Pietras et al., "Antibody to HER–2/neu receptor blocks DNA repair after cisplatin in human breast and ovarian cancer cell", 1994, Oncogene 9:1829–38.

Van Diest et al., "Quantitation of HER–2/neu oncoprotein overexpression in invasive breast cancer by image analysis: a study comparing fresh and paraffin–embedded material", Analytical Cellular Pathology, vol. 3, No. 4, 1991, pp. 195–202.

Vincent et al., "Anticancer efficacy of the Irreversible EGFr Tyrosine Kinase Inhibitor PD 0169414 Against Human Tumor Xenografts", 2000, Cancer Chemother. Pharmacol. 45:231–38.

DiGiovanna, 1999, PPO Updates: Princ. Practice Oncol. 13:1–9.

Shak, 1999, Semin. Oncol. 26:71–77.

Sliwkowski et al., 1999, Semin. Oncol. 26:60–70.

* cited by examiner

METHOD FOR QUANTITATING A PROTEIN BY IMAGE ANALYSIS

This application is a continuation of U.S. Provisional Patent Application Nos. 60/176,514 and 60/176,515, each filed on Jan. 12, 2000, the disclosure of each of which is explicitly incorporated by reference herein.

BACKGROUND OF THE INVENTION

1. Field of the Invention

This invention relates to a method for determining the level of expression of a target protein in a tissue or cell sample. Specifically, the invention relates to a method for determining the level of expression of a target protein in a tissue or cell sample using image analysis.

2. Background of the Invention

In aiding a clinician in the diagnosis of cancer, a pathologist faces two key problems. First, the pathologist must determine whether a tissue or cell sample removed from a patient is benign or malignant. Second, upon reaching a determination that the tissue or cell sample is malignant, the pathologist must then classify the aggressiveness of the cancer and determine its clinical and biological behavior.

A diagnosis of cancer must be confirmed through histological examination of a tissue or cell sample removed from a patient. Such histological examination entails tissue-staining procedures that allow the morphological features of the tissue to be readily examined under a light microscope. The pathologist, after having examined the stained tissue or cell sample, makes qualitative determinations of the state of the tissue or the patient from whom the sample was removed and whether the tissue is benign or malignant. The aggressiveness of the tumor, however, is difficult to ascertain using standard histological techniques. The clinician uses the pathologist's histological analysis to select a suitable treatment, balancing the resistance or responsiveness of the cancer to therapy with the potential harm to the patient resulting from the selected therapy (Muss et al., 1994, *N. Engl. J. Med.* 330:1260–66).

Visual examination of tissue and cell samples is often augmented by the use of an automated (computer-aided) image analysis system. A representative system includes a computer that receives a magnified image of the tissue or cell sample from a television camera and processes the received optical image. Image analysis is generally used to assess the affinity of stains for various biological markers. Examples of suitable affinity stains include chromagen-labeled monoclonal antibodies directed against the estrogen receptor (ER), the progesterone receptor (PR), the HER-2/neu protein, and the epidermal growth factor receptor (EGFR).

The coupling of affinity staining and computer-aided image analysis has permitted clinicians to better select optimal therapies for their patients (e.g., hormone therapy for cancers that are ER and PR positive and anti-oncogene receptor therapy—such as using monoclonal antibodies directed against to HER-2/neu (Herceptin™), EGFR, or C225™, alone or in combination with chemotherapy). In addition, image analysis techniques can be used to quantitate other receptors such as those in the erbB receptor family (HER-1, HER-2/neu, HER-3, and HER-4), their ligands (EGF, NDF, and TGFα), and downstream signals (PI3 kinase, Akt, MAP kinase, and JUN kinase) (National Institute of Health Consensus Development Conference: Steroid Receptors in Breast Cancer, 1979, Vol. 2 No. 6; Kraus et al., 1989, *Proc. Natl. Acad. Sci. U.S.A.* 86:9193–97; Mendelsohn, 1990, *Semin. Cancer Biol.* 1:339–44; Hancock et al., 1991, *Cancer Res.* 51:4575–80; Peles et al., 1991, *EMBO J.* 10:2077–86; Peles et al., 1992, *Cell* 69:205–16; Arteaga et al., 1994, *Cancer Res.,* 54:3758–65; Pietras et al., 1994, *Oncogene* 9:1829–38; Baselga et al., 1999, Proceedings of AACR NCI EORTC International Conference, Abstract 98; Cobleigh et al., 1999, *J. Clin. Oncol.* 17:2639–48; DiGiovanna, 1999, *PPO Updates: Princ. Practice Oncol.* 13:1–9; Shak, 1999, *Semin. Oncol.* 26:71–77; Sliwkowski et al., 1999, *Semin. Oncol.* 26:60–70; Vincent et al., 2000, *Cancer Chemother. Pharmacol.* 45: 231–38).

When a tumor sample is examined using immunohistochemical analysis alone, accurate quantitation of a specific target protein being expressed by the tumor cells is often hampered by the presence of normal tissue that is removed from the patient with the tumor sample. Biological approaches for the treatment of cancer, such as the use of monoclonal antibodies or kinase inhibitors, rely on accurate quantitation of specific target proteins in a tumor sample. For example, the effectiveness of the HER-2/neu antibody Herceptin™ has been shown to depend on the amount of HER-2/neu being expressed in tumor cells (Table 1).

There remains a need in the art to develop more accurate methods for determining the level of expression of a target protein in a tissue or cell sample. The development of such methods would have wide application in the treatment of cancer.

SUMMARY OF THE INVENTION

The present invention provides methods for determining the level of expression of a target protein in a tissue or cell sample. The invention specifically provides methods for determining expression levels for a target protein in a tissue or cell sample using image analysis. In the method of the present invention, a computer-aided image analysis system is used to enhance and process optical images of an immunohistochemically stained tissue or cell sample, and to determine the optical density of the stained tissue or cell sample.

In one method of the present invention, the level of expression of a target protein in a sample cell is determined by immunohistochemically staining the cells in the sample and at least a first control cell and a second control cell using a detectably-labeled antibody directed against the target protein, wherein the level of expression of the target protein in the first and the second control cells is known, and wherein the level of expression of the target protein in the first and second control cells is not the same, determining the optical density of the stained sample cell and stained first and second control cells, generating a calibration curve from the determinations of the optical density of the first and second control cells, and determining the level of expression of the target protein in the sample cell using the generated calibration curve. In preferred embodiments, the detectable label is a chromagen or a fluorophore.

The method of the present invention offers several advantages over techniques disclosed in the prior art. For example, in the method of the present invention, the level of expression of a target protein may be assayed in the tumor cells of a tissue sample (excluding normal tissue removed from the patient with the tumor sample), thus generating a more meaningful quantitation of the specific target protein within the tissue sample. Furthermore, the method of the present invention overcomes the problems associated with cell staining variability that result from variations in staining conditions (for example, when the level of expression of a target protein is determined by ELISA assay; see FIGS. 1A–1D).

Specific preferred embodiments of the present invention will become evident from the following more detailed description of certain preferred embodiments and the claims.

DETAILED DESCRIPTION OF THE PREFERRED EMBODIMENTS

The methods of the present invention are useful for accurately determining expression levels of a target protein in a tissue or cell sample using image analysis. Specifically, the present invention provides methods for determining expression levels of a target protein in a tissue or cell sample using a computer-aided image analysis system to enhance and process optical images of an immunohistochemically stained tissue or cell sample, and to determine the optical density of the stained tissue or cell sample. More specifically, the present invention provides a method for determining the level of expression of a target protein in the tumor cells of a tissue or cell sample removed from a patient.

In one embodiment of the methods of the present invention, expression levels of a target protein in a sample is determined by immunohistochemically staining cells in the sample and at least a first control cell pellet and a second control cell pellet using a detectably-labeled antibody directed against the target protein, wherein the expression level of the target protein in the first and the second control cell pellets is known (for example, after determination by methods known in the art such as, inter alia, ELISA), and wherein the expression level of the target protein in the first and second control cell pellets is not the same; determining the optical density of the stained sample cell and stained first and second control cell pellets, generating a calibration curve from the determinations of the optical density of the first and second control cell pellets, and determining the expression level of the target protein in the sample cells using the generated calibration curve. In preferred embodiments, the detectable label is a chromagen or a fluorophore.

In the practice of the methods of the invention, the amount of target protein in a biological sample is quantitated (i.e., the amount determined) using calibration curves that relate the amount and degree of target protein-specific staining to the amount of the target protein in the sample. This is most generally accomplished by using cells, most preferably cultured cell lines that produce a consistent amount of the target protein that can be determined with high degrees of accuracy and precision. In preferred embodiments, a plurality of cell populations are assayed that each express different amounts of the target protein. Such cell populations are used to determine the amount of target protein-specific staining associated with varying amounts of target protein in the different cell populations. Examples of the results of such calibration experiments are shown in Table 7, wherein is provided a comparison of determinations of the amount of HER-2/neu by ELISA and by image analysis as described herein. In certain preferred embodiments the amount of target protein-specific staining is normalized or expressed relative to the amount of total cell protein, to provide a convenient measure for analyzing biological tissues, preferably tumor tissue and most preferably malignant tumor tissue, in which a determination of cell number would be impractical or unreliable. In the practice of the invention, the correlation between target protein-specific staining and the amount of target protein expressed in a cell is expressed as a calibration curve relating the amount of target protein to a physical parameter, most preferably optical density, associated with target protein-specific staining. The calibration curves produced according to and used with the methods of the invention are also advantageously expressed as an algorithm, most preferably in the form of a linear or logarithmic equation.

Target proteins can be detected using a specific reagent, most preferably an antibody, that is itself detectably labeled, or using an unlabeled, target protein-specific antibody and a second antibody that is detectably labeled and recognizes the target protein-specific antibody. Alternatively, any molecule that can be detectably labeled and that specifically binds to the target protein can be used in the practice of the methods of the invention. In a preferred embodiment of the methods of the present invention, a two-component immunohistochemical staining system is used to differentially stain the target protein and the tissue or cell sample so that the stained target protein can be more readily distinguished from the counterstained tissue or cell sample. For example, the target protein can be stained using diaminobenizidine (DAB) and the tissue or cell sample can be counterstained using ethyl green or methylene blue. Following immunohistochemical staining, the optical image of the tissue or cell sample generated by the computer-aided image analysis system is then magnified under a light microscope and separated into a pair of images. The separated images are enhanced using a pair of optical filters, one having a maximum absorption corresponding to the stain and the other having a maximum absorption corresponding to the counterstain. In other embodiments of the method of the present invention, a plurality of image analysis filters are used to detect, differentiate, and quantitate the level of staining of different cellular proteins in various components (e.g., membrane, cytoplasm, and nucleus).

In a preferred embodiment of the methods of the present invention, stain and counterstain lot variability is controlled by using the same reagents to stain the sample cells and first and second control cell pellets. In another preferred embodiment of the methods of the present invention, environmental differences and variability in the staining procedure are controlled for by staining the sample cells and first and second control cell pellets at the same time.

In preferred embodiments, target protein-specific staining is detected, measured and quantitated using image analysis equipment, defined herein as comprising a light or fluorescence microscope, and image-transmitting camera and a view screen, most preferably also comprising a computer that can be used to direct the operation of the device and also store and manipulate the information collected, most preferably in the form of optical density of certain regions of a stained tissue preparation. Image analysis devices useful in the practice of this invention include but are not limited to the CAS 200 system (Becton Dickenson, Mountain View, Calif.).

The inventive methods are practiced on such an image analysis system as follows. After immunohistochemical staining, a quantified measure of the percentage of expressing cells can be taken by digitizing microscope images of stained samples, and converting light intensity values in each picture element (pixel) of the digitized image to optical density values, which correspond to the percentage of stained cell nuclei.

More specifically, computerized image analysis can be used to determine from a digital grey scale image, a quantity of cells having a particular stain. The grey scale images are representative of the amount of an optical enhancement factor, such as a chromagen, which binds to a specific target under study and thereby allows optical amplification and visualization of the target.

An apparatus for utilizing computerized image analysis includes a means for magnifying and displaying the image of a group of cells of a specimen from a field on a microscope slide. The specimen cell population is prepared with special staining and counterstaining technique using immunohistochemical or any other enzymatic staining methods known in the art. Appropriate stains and counterstains are selected by their ability to distinguish between cells containing the antibody sandwich complexes of specific enzymes or markers and those that do not contain such complexes through cameras used with the computerized image analysis system. After staining, the image field is digitized by the apparatus and stored in a memory provided by the system. From the digitized image, a nuclear or cytoplasmic image mask is formed by forming the image at one wavelength of light such as red wavelength or green optical filter. The tissue mask is stored and a second filter is used to form another filtered image of the areas with the optical enhancement factor. Differentiation of cellular characteristics can be made by comparing the first image with the second image to obtain a quantification of material stained with the optical enhancement factor and thus, an assay of the amount of the particular target under study.

In a first step, any expressed target protein in the cells is identified by adding a detectably-labeled primary antibody specific for the target protein, or alternatively an unlabeled primary antibody and a detectably-labeled secondary antibody specific for the primary antibody. The antibodies are incubated with the sample for a time to form complexes if these antigens are present.

The complexes are then visualized by treating the sections with a stain such as diaminobenizidine (DAB) stain under appropriate conditions. In a second step, the tissue is counterstained with another optical enhancement factor, for example ethyl green. Although a staining technique using peroxidase and ethyl green is exemplary, other stains and optical enhancement factors are also suitable such as alkaline phosphatase based with specific chromagens such as Fast Red, Fast Green, etc. Spectral studies have shown that the ethyl green stain offers good spectral separation from the DAB precipitate of the immunoperoxidase technique such that different features of the image can be readily separated by filtering it at two different wavelengths. This allows the image to be digitized into two separate images, one in which all the cell nuclei are optically enhanced (ethyl green or Fast Green) and one in which only those tissue areas with receptor staining (DAB) are optically enhanced. In a preferred embodiment, the images can be separated by a 600 nanometer (red) filter to produce an image of all of the counter stained area, and a 500 nanometer (green) filter to produce an image of only those tissue areas with the DAB precipitate staining.

To further differentiate those areas, an interactive threshold setting technique can be used where an operator visualizing the images can set a boundary on the areas under consideration. When the boundaries are set, the images are formed by eliminating all parts of the image that are below the thresholds in optical density. A threshold is set for the first image, and a second threshold is set for the second image.

The image processing method then consists of first forming the mask image of the tissues under consideration with the red filter. This mask image is stored and another image for expressed protein quantification is then acquired by using the green filtered version of the same image. The effect of the filters in combination is to optically enhance (make darker) those areas of the tissue mask where tissue components are stained with DAB and to make lighter those tissue components with only green counterstain. An image analysis can then be performed using only those areas of the image that are stained and which are within the mask.

Statistical analysis of the differences between, and comparison of the two images such as a histogram, is used to quantitate the amount. Also, the proportion or percentage of total tissue area stained may be easily measured, as the area stained above an antibody threshold level in the second image.

Red and green filters are suitable for practice of the invention as well as DAB and green counterstain. This implementation shows a convenient and advantageous method for discriminating between two areas having counterstaining. It is recognized that there are various other staining or optical enhancement methods and filtering methods which can be used to optically enhance one particular area or feature over another cell feature such as Fast green, eosin, and the like.

The method of the present invention is particularly useful for determining the level of expression of receptor proteins such as the estrogen receptor (ER), the progesterone receptor (PR), the HER-2/neu protein, and the epidermal growth factor receptor (EGFR), as these proteins play a major role in determining specific biological therapeutic approaches (e.g., monoclonal antibodies or kinase inhibitors) (Bacus et al., 1997, *Anal. Quant. Cytol. Histol.* 19:316–28; Bacus et al., 1999, *Breast J.*). Examples of such determinations are shown in Tables 8A and 8B, where the results of image analysis according to the invention are reported as $fmol/\mu g$ and number of HER-2/neu receptors per cell. The method of the present invention is also suitable for determining the level of expression of other receptors, including the HER family of receptors, their ligands, and other nuclear antigens, and signal transduction receptors (e.g., P13K/Akt, MAPk, and JUN kinase). Exemplary results of determinations using HER-4 are shown in Table 9.

A preferred embodiment of the methods of the present invention and its advantages over previously investigated methods for determining the level of protein expression in tissue or cell samples are best understood by referring to FIGS. 1–6 and Examples 1–2. The Examples, which follow, are illustrative of specific embodiments of the invention, and various uses thereof. They are set forth for explanatory purposes only, and are not to be taken as limiting the invention.

EXAMPLE 1

Quantitation of Target Proteins by Enzyme Linked Immunosorbant Assay (ELISA)

Sandwich enzyme immunoassays, utilizing a mouse monoclonal capture antibody and a rabbit polyclonal detection serum, were used to determine the level of expression of HER-2/neu, EGFR, ER, or PR in control tissues and cells. ELISA assays were performed using commercially available kits (Abbott Laboratories, North Chicago, Ill. Calbiochem, La Jolla, Calif.). ELISA assays were conducted so that the intensity of the calorimetric reaction obtained for individual tissue or cell samples did not fall outside the working range of the assay.

While performing ELISA assays, tissue and cell samples were kept at 0–4° C. Cell pellets were weighed, suspended in 10 volumes of cold Receptor Buffer (10 mM Tris-HCl, pH 7.4, 1.5 mM EDTA, 10% glycerol, 0.1% sodium azide, 0.5 $\mu g/ml$ pepstatin, 0.2 mM pA-PMSF), and then homogenized for 5 seconds using a Tekrnar Tissuemizer. Following incubation on ice for 15–20 seconds, samples were again homogenized for 5 seconds. Tissue samples were minced prior to suspension in Receptor Buffer. Following homogenization, Antigen Extracting Agent (AEA) was added to the homogenates (10 $\mu l$ of AEA for every 50 $\mu l$ of homogenate), the samples were mixed, and then the samples were stored at −70° C. until ELISA assays were performed.

Prior to ELISA analysis, the homogenates were centrifuged at 15,000 rpm for 15 minutes at 4° C. and the supernatants were then transferred to fresh tubes. Protein levels for each supernatant were determined using the method of Lowry et al. (1951, *J. Biol. Chem.* 193: 265–275) and the samples were diluted to 5 $\mu g/ml$ total protein. Samples were then loaded into the wells of a 64-well microtiter plate provided with the ELISA kit. All samples were assayed in duplicate. The level of expression of HER-2/neu (in $fm/\mu g$ of total protein) was determined by dividing the amount of HER-2/neu as calculated in the ELISA assay by the amount of total protein as calculated above.

The levels of EGFR, ER, and PR expression were determined as described above for the determination of HER-2/neu expression.

In selecting control cells for the generation of a calibration curve, biologically engineered cells such as MCF7/HER-2 cells (Peles et al., 1991, *EMBO J.* 10:2077–86) or Chinese hamster ovary cells (CHO) transfected with HER-2/neu or EGFR expression constructs are preferable due to their more constant expression of HER-2/neu or EGFR.

EXAMPLE 2

Quantitation of Target Proteins by Image Analysis

To assess the method of the present invention, the level of expression of HER-2/neu, ER, or PR in a number of tumor tissues was quantitated by image analysis. Tissue samples which had been previously shown by other methods to be HER-2/neu, ER, and PR negative or express varying amounts of HER-2/neu, ER, and PR positive tumor and normal cells (covering a response range of 0 $fmol/mg$ to over 500 $fmol/mg$ target protein) were used in the analysis.

Target protein expression in tissue or cell samples was quantitated using equations derived from calibration curves generated from ELISA assay and image analysis of control (calibrator) cells. Control cells were stained and quantitated in parallel with the tissue or cell samples to be analyzed. The reproducibility of target protein quantitation in control cells by ELISA assay and image analysis was assessed as follows.

Control cell pellets were first divided into four fractions, the concentration of ER was determined in two fractions by ELISA assay, and the optical density of ER staining was determined in two fractions by image analysis. Table 2 shows that reproducible measurements of ER concentration and optical density were obtained by ELISA assay and image analysis, respectively.

To quantitate ER expression in tumor tissue samples, a calibration curve was generated by graphically representing the concentration (in fmol/equivalent or receptors per cell) of the target protein in three control cell pellets as determined by ELISA assay (performed as described in Example 1) with the average optical density of these pellets as determined by image analysis. The average sum optical density per pixel, which corresponds to the total number of pixels comprising the membrane or nuclear area of a tissue sample, was calculated by dividing the total optical density of the stained target protein by the total number of pixels of the ethyl green or methylene blue stained sample. The results of both ELISA assay and image analysis of the tumor tissue samples is shown in Table 3. ELISA values listed as ">" fmol/mg were obtained from tissues in which the expression of the target protein fell outside the limits of detection by the ELISA assay. The levels of ER expression as determined by ELISA assay and image analysis correlated with the levels of ER expression as determined using other methods.

Figure 1A:
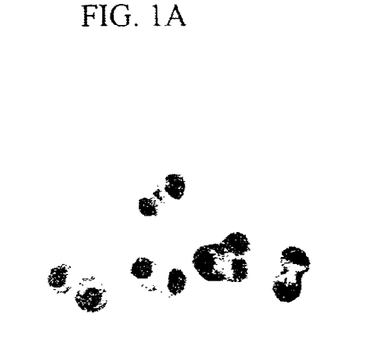
FIGS. 1A–1D are photomicrographs of cells stained under different conditions of immunohistochemical analysis of HER-2/neu expression in transfected MCF-7 cells expressing HER-2/neu. QDL Callibrator cells (1A and 1B) and transfected MCF-7 cells (1C and 1D) were stained for 3 minutes at room temperature (1A and 1C) or for 5 minutes at 37° C. (1B and 1D), using the alkaline phosphatase method, with variable results in staining intensity. However, using calibration curves as shown in FIG. 2, accurate quantitation of receptor (0.19 pg/cell) are obtained under different staining conditions for the same cells.
Figure 1B:
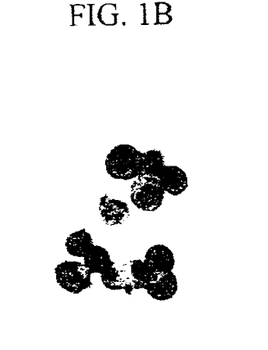
Figure 1C:
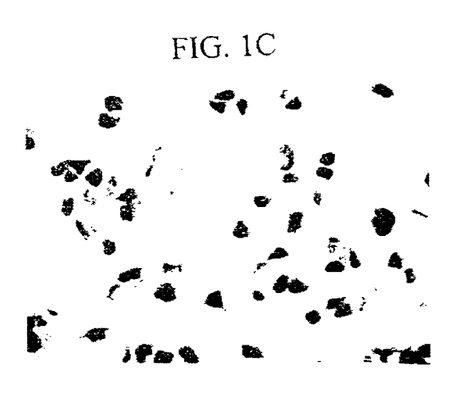
Figure 1D:
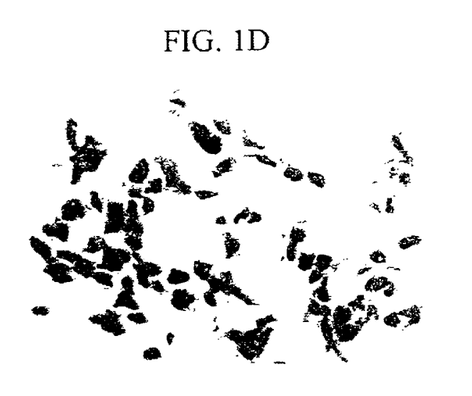
Figure 2:
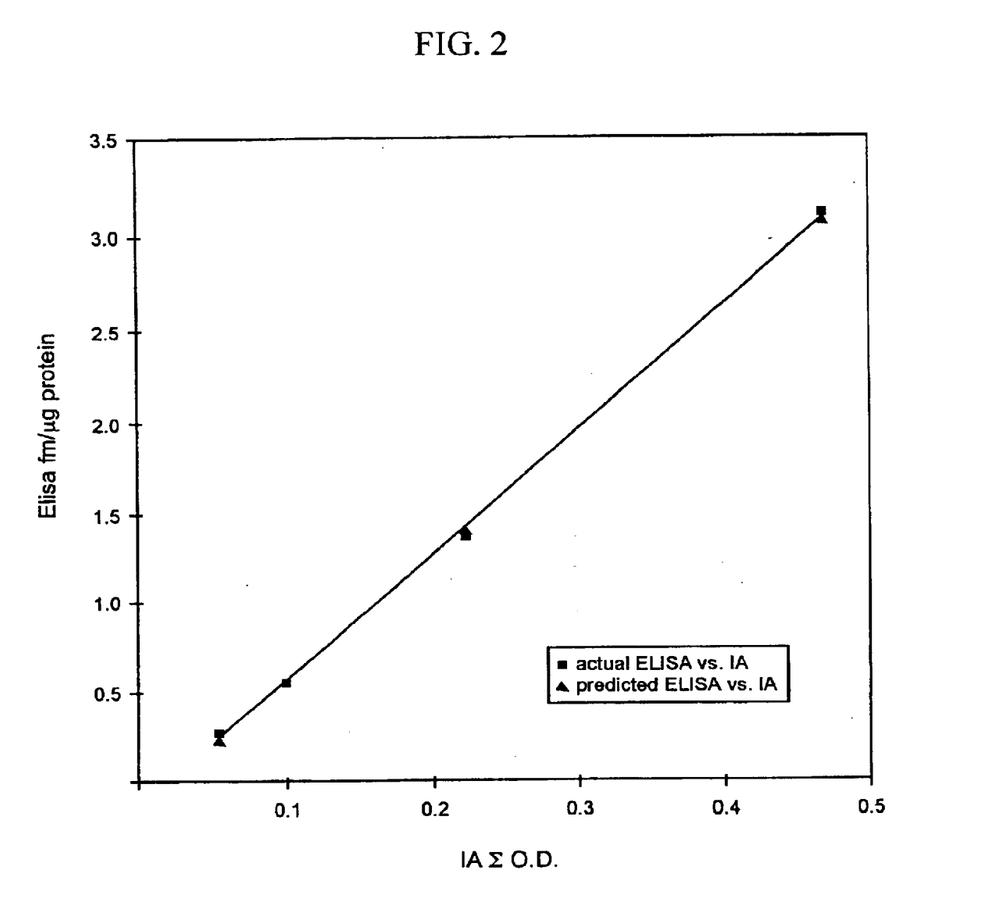
FIG. 2 is a graph showing the relationship between the amount of HER-2/neu in a cell pellet (expressed as femtomoles/microgram protein as determined by ELISA) and the pixel average of the optical density of HER-2/neu staining as determined by image analysis in cells expressing known amounts of HER-2/neu.
Figure 3:
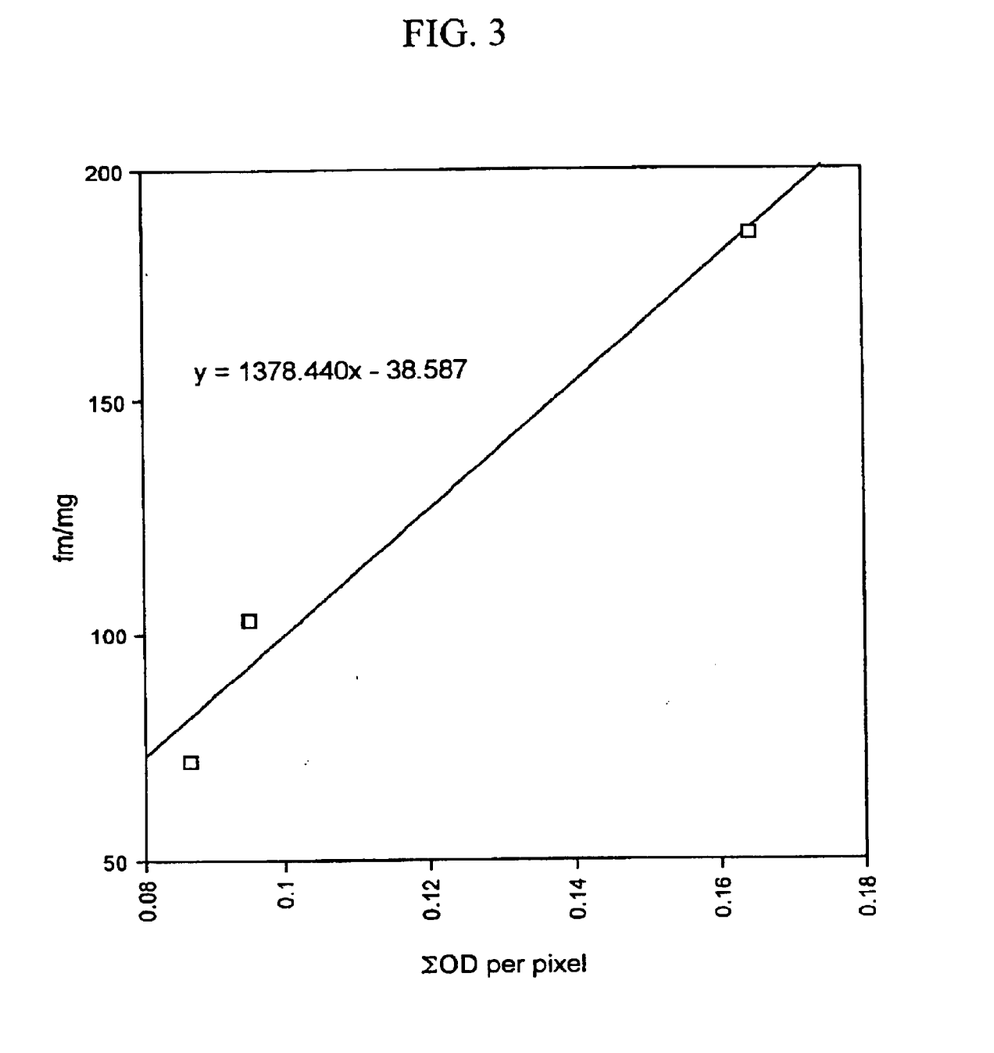
FIG. 3 is a graph showing the relationship between the amount of estrogen receptor (ER) in a cell pellet (expressed as femtomoles/microgram protein as determined by ELISA) and the pixel average of the optical density of ER staining as determined by image analysis in cells expressing known amounts of ER.
Figure 4A:
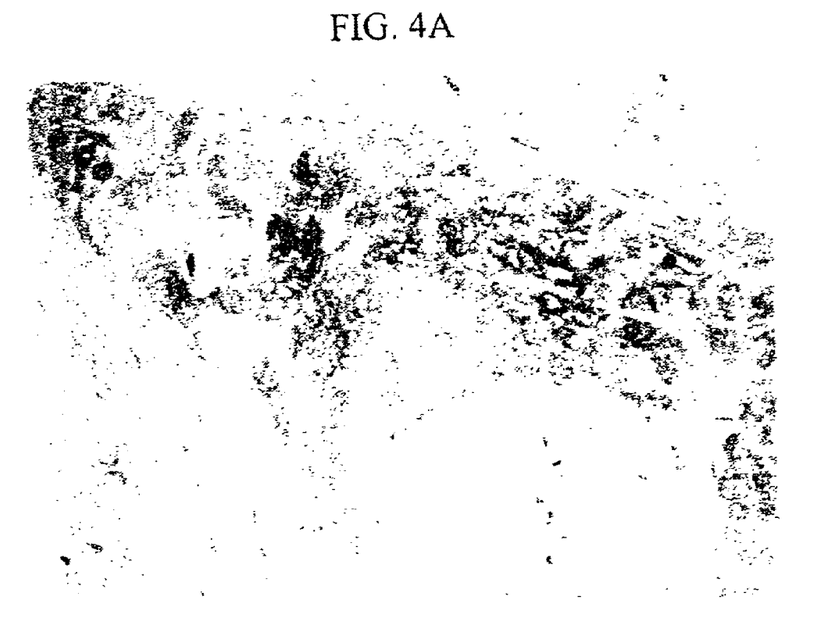
FIGS. 4A–4B are photomicrographs of immunohistochemical analyses of epidermal growth factor receptor (EGFR) expression in breast and bladder tumors. Tissue samples were stained using the alkaline phosphatase method.
Figure 4B:
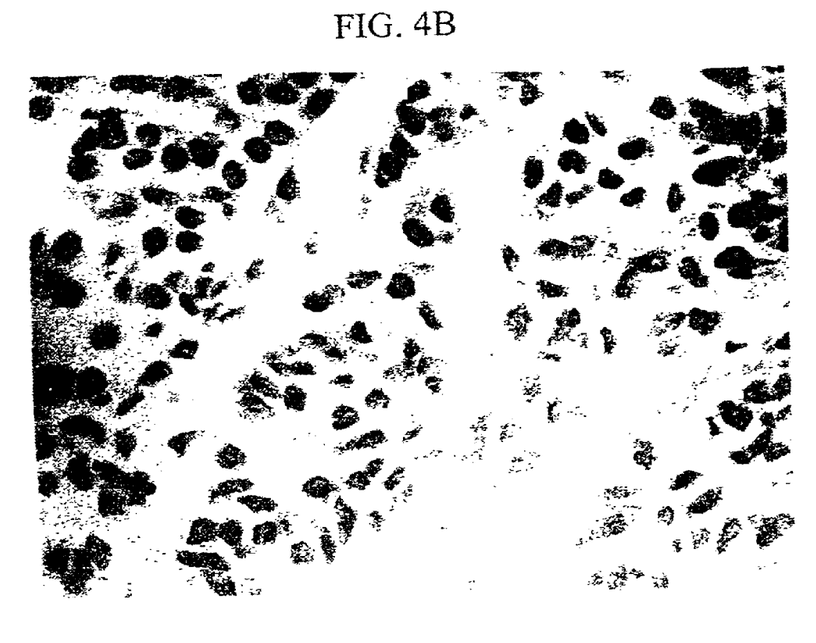

In another experiment, three frozen control cell pellets, known to express either ER or HER-2/neu, were sectioned and stained along with several frozen tissue section samples. The level of ER or HER-2/neu expression in the control cell pellets (in fmol/mg total protein) was determined by ELISA assay. Control cell and tissue sections were then stained and the slides quantitated using image analysis to determine the average optical density and percentage of HER-2/neu or ER staining. Calibration curves were generated by plotting the average optical density of the stained control cells, as determined by image analysis, against the concentration of the target protein (in fmol/mg total protein), as derived by ELISA assay. FIGS. 2 and 3 illustrate the calibration curve generated from HER-2/neu and ER expressing control cells. The equations from these graphs were used to quantitate ER or HER-2/neu expression in tissue samples. The results of both ELISA assay and image analysis of the tumor tissue samples is shown in Table 4.

The results above indicate that the method of the present invention can be used to accurately quantitate the level of expression of receptor proteins being expressed in tumor cells. However, the concentration of the target protein as determined by ELISA assay for some tumor samples did not directly correlate with the concentration of the target protein as determined by image analysis. As the result of normal cells present in the tumor sample, target protein quantitation by ELISA assay may yield concentrations that are lower or higher than those obtained by image analysis. For example, the presence of normal cells that do not express the target protein (e.g., HER-2/neu, ER, or PR) can dilute the ELISA value. This phenomenon is illustrated by tissue sample 98–594 (Table 4), wherein the concentration of target protein as determined by ELISA assay was significantly lower than that as determined by image analysis. Alternatively, the presence of normal cells expressing the target protein (e.g., normal breast ducts expressing HER-2/neu, ER, or PR) can significantly increase the levels of HER-2/neu, ER, or PR as quantitated by ELISA assay. Where extracted tumor samples comprise tumor cells and surrounding normal duct tissue, an ELISA assay may yield higher levels of target protein expression when, in fact, the tumor cells actually express lower levels of target protein (Table 3).

To assess the capability of the method of the present invention for quantitating other receptors (such as HER-3, HER-4, their ligands, and other factors), image analysis was performed on samples removed from patients who had received Doxorubicin-based chemotherapy (Esteva et al., 2001, submitted to *Pathology Oncology Research*). Table 5 gives the range of optical density units as observed for HER-3, HER-4, Heregulin, and the factor p38 (DiGiovanna, 1999, *PPO Updates: Princ. Practice Oncol.* 13:1–9).

Using the method of the present invention, the prognostic role of antibodies directed against HER-4, Heregulin, and phosphorylated p38 (P-p38) (Santa Cruz, Santa Cruz, Calif.) was analyzed in paraffin-embedded breast cancer tissue removed from 35 patients. Patients whose tumors expressed high levels of HER-4 and Heregulin had a worse 5-year disease free survival (DFS) as compared to patients whose tumors expressed low levels of these proteins. The opposite was noted for phosphorylated p38 where high levels of protein expression were associated with improved DFS. No correlation was observed between other markers and survival in this small subset of patients. The associations noted between the expression of HER-4, Heregulin, and P-p38 and DFS were not explained by other known prognostic factors. In conclusion, the results obtained by image analysis suggest that HER-4, Heregulin, and P-p38 have prognostic value in patients with early stage breast cancer (Esteva et al., 1999, *Clinical Cancer Res.*). The importance of accurate quantitation of the expression of such target proteins is shown in Table 1, as tumors possessing level 3 expression of HER-2/neu respond better to Herceptin.

The method of the present invention was also used to quantitate EGFR in various cell lines (results shown in Table 6A) and tumor samples (results shown in Table 6B). With EGFR, the image analysis methodology was used to determine the number of receptors per cell.

Figure 5A:
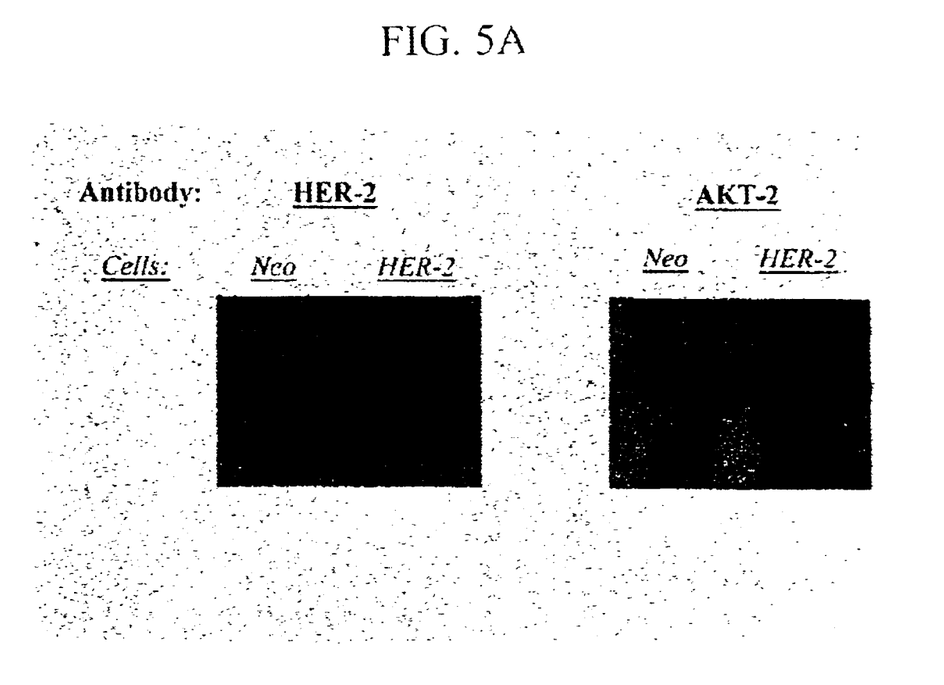
FIGS. 5A–5C are photographs of autoradiograms of Western blot analysis of HER-2/neu (HER-2) and Akt-2 (AKT-2) expression in MDA-MB453 cells transfected with HER-2/neu (HER-2) or a control (Neo) vector (5A); immunohistochemical analysis of HER-2/neu (2114 HER-2 IHC) or Akt-2 (2114 AKT2 IHC) or fluorescent in situ hybridization (FISH) analysis (2114 HER-2 FISH) in a patient tissue sample (5B); and the correlation between HER-2/neu and Akt-2 expression in tumor samples as determined by image analysis (5C)
Figure 5B:
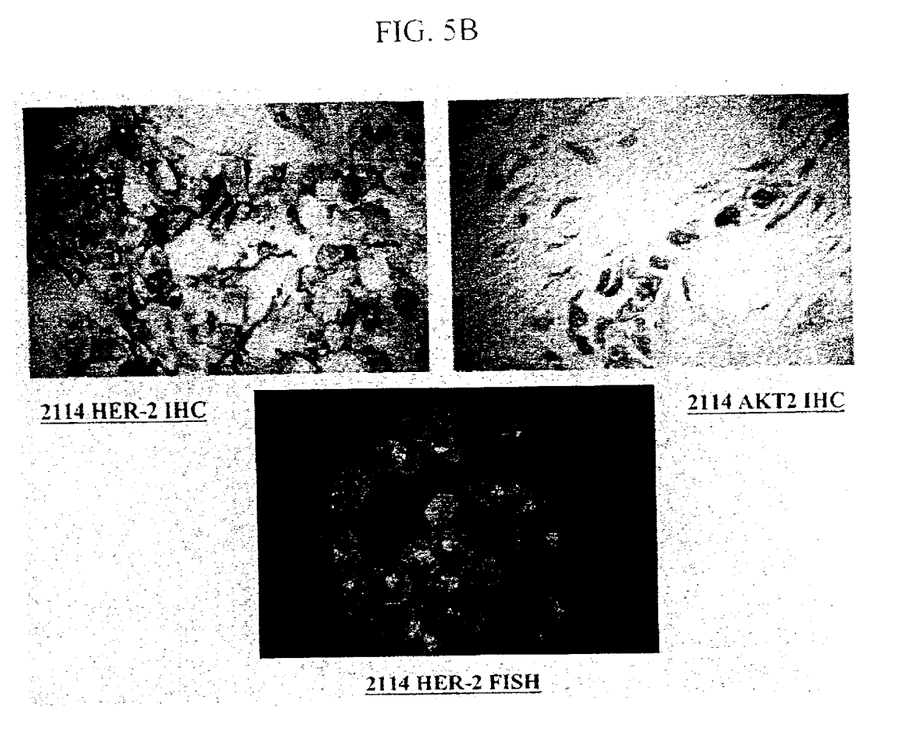
Figure 5C:
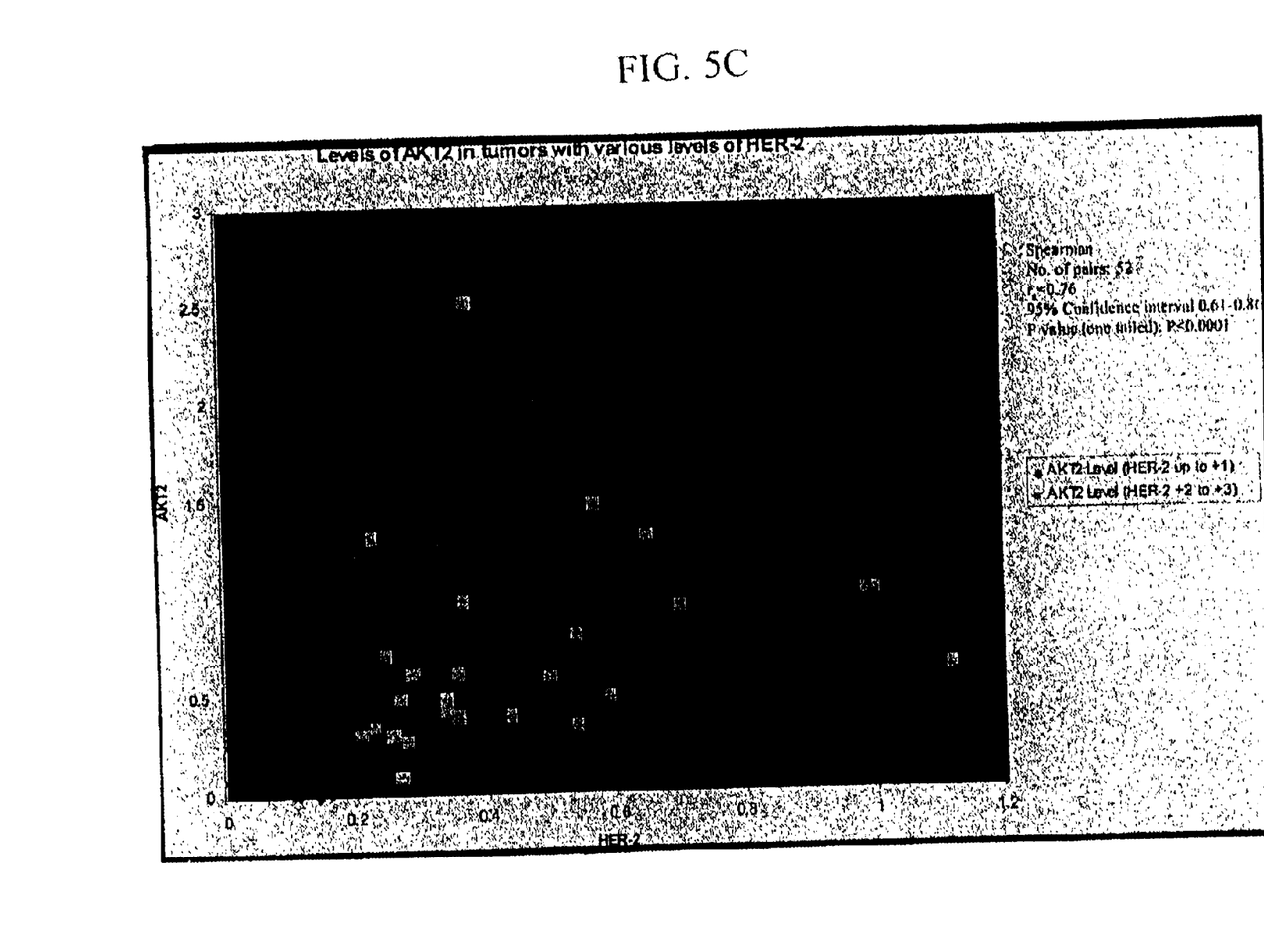
Figure 6:
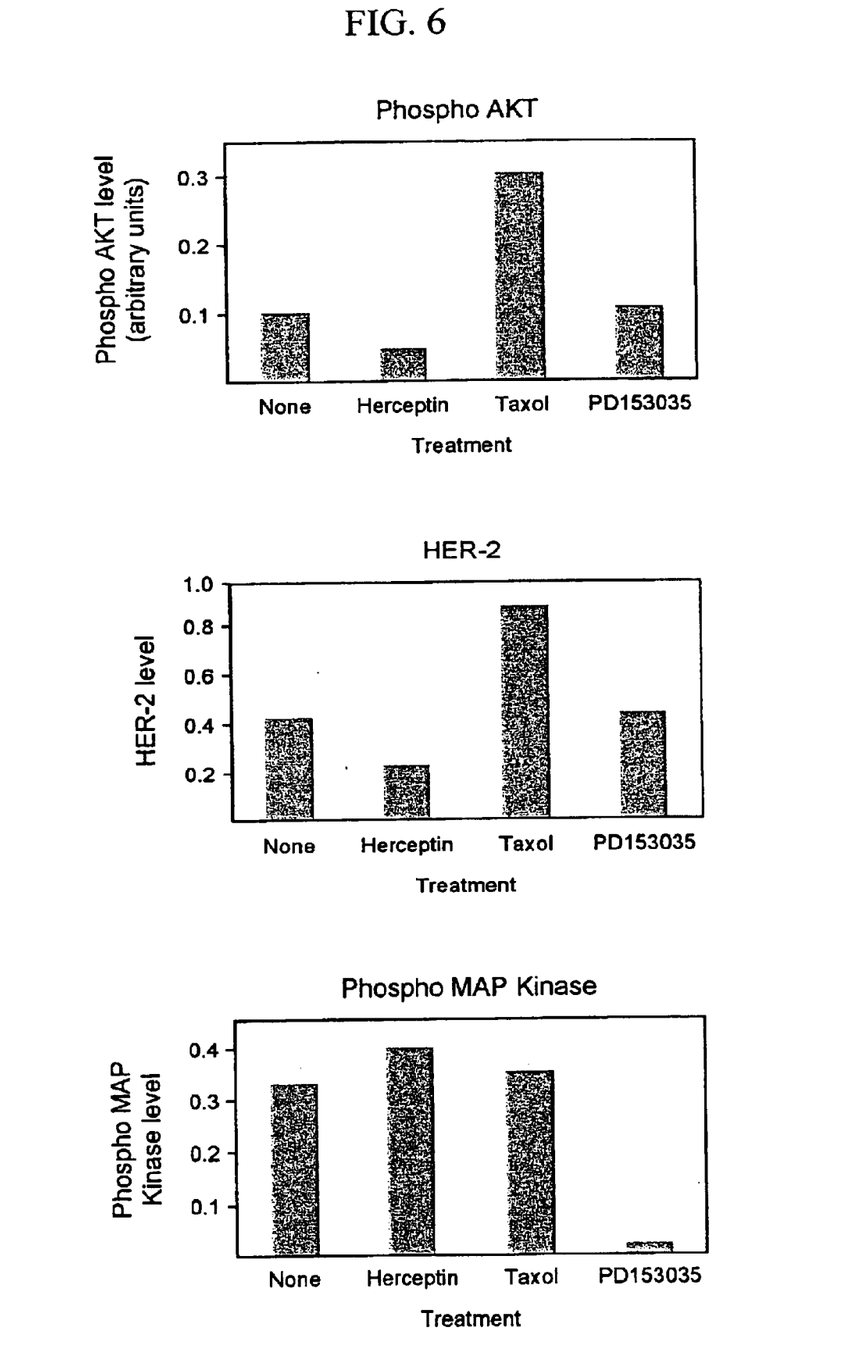
FIG. 6 are histograms showing the results obtained for image analysis of activated Akt (Phospho AKT), HER-2/neu (HER-2), or activated MAP kinase (Phospho MAP Kinase) in cells treated with Herceptin, Taxol, or PD153035.

Finally, image analysis was used to examine the expression of target proteins involved in signal transduction pathways and to correlate the expression levels of these target proteins with the expression of oncogenes such at Akt-2 and HER-2/neu or with drug response (such as the downregulation of pAKT or MAPk following Herceptin treatment). FIGS. 5 and 6 illustrate that by using image analysis, the upregulation or downregulation of target proteins involved in signal transduction can be correlated with the expression of oncogene proteins such as HER-21neu and Akt-2. Using image analysis, it can be shown that HER-2/neu overexpression in tumors is associated with the overexpression of Akt-2, which likely contributes to the aggressive nature of these cancers.

It should be understood that the foregoing disclosure emphasizes certain specific embodiments of the invention and that all modifications or alternatives equivalent thereto are within the spirit and scope of the invention as set forth in the appended claims.

TABLE 1

Treatment Effect Versus Level of Her-2 Expression

| | Single-Arm Trial Herceptin ™ | Treatment Subgroups in Randomized Trial | | | |
|---|---|---|---|---|---|
| | | Herceptin ™ + Paclitaxel | Paclitaxel | Herceptin ™ + AC | AC |
| | Overall Response Rate | | | | |
| 2 + Overexpression | 4% (2/50) | 21% (5/24) | 16% (3/19) | 49% (14/35) | 43% (18/42) |
| 3 + Overexpression | 17% (29/172) | 44% (30/68) | 14% (11/77) | 53% (57/108) | 36% (35/96) |

TABLE 2

| Pellets | Fmol/mg ELISA | Fmol/mg Image Analysis |
|---|---|---|
| MCF7 2 12167 | 220.0 | 262.0 |
| MCF7 1 12167 | 236.0 | 307.0 |
| MCF7 2 01148 | 188.0 | 183.0 |
| MCF7 3 01148 | 179.0 | 207.0 |
| ERC 1 01148 | 348.0 | 315.0 |
| ERC 3 01158 | 358.0 | 338.0 |

TABLE 3

Correlation between ELISA and Image Analysis Values of Estrogen Receptor in Patient Tissues

| Tissue | Fmol/mg ELISA | Fmol/mg Image Analysis | % Positive Area Image Analysis |
|---|---|---|---|
| 95-1014 | 62 | 70 | 25 |
| 95-1052 | 23 | 36 | 43 |
| 95-1071 | 186 | 105 | 45 |
| 96-1130 | 34 | 34 | 0.6 |
| 96-1142 | 35 | 122 | 51 |
| 96-1268 | 170 | 150 | 34 |
| 96-328 | >250 | 238 | 45 |
| 96-361 | 109 | 85 | 40 |
| 97-029 | 256 | 91 | 36 |
| 97-1161 | >167 | 240 | 65 |
| 97-1234 | >294 | 262 | 51 |
| 97-1275 | 21 | 93 | 41 |
| 97-1350 | 226 | 217 | 55 |
| 97-1469 | 38 | 56 | 26 |
| 97-1497 | 0.5 | 0 | 0 |
| 97-234 | 2.5 | 0 | 0 |
| 97-242 | 27 | 40 | 6 |
| 97-573 | 11.5 | 33 | 2 |
| 98-011 | 135 | 77 | 27 |
| 98-025 | >454 | 556 | 78 |
| 98-035 | 143 | 150 | 46 |
| 98-043 | 25 | 114 | 47 |
| 98-077 | >227 | 318 | 65 |
| 98-078 | 305 | 23 | 2 |
| 98-087 | 56 | 55 | 23 |
| 98-098 | 77 | 73 | 26 |
| 98-103 | 178 | 160 | 15 |
| 98-134 | 304 | 10 | 0.2 |
| 98-159 | 10 | 18 | 0.2 |
| 97-341 | >161 | 191 | 70 |
| 97-417 | 90 | 125 | 19 |
| 97-446 | 250 | 201 | 55 |
| 97-647 | 0.94 | 0 | 0 |
| 97-1053 | 76 | 71 | 14 |
| 97-1111 | 273 | 217 | 56 |

TABLE 4

Results of HER-2/neu ELISA and HER-2/neu Quantitative Image Analysis (IA) on Five Breast Cancer Tissues

| Tissue I.D. | ELISA fm/μg | IA fm/μg |
|---|---|---|
| 98-510 | 0.23 | 0.30 |
| 98-511 | 1.74 | 1.12 |
| 98-551 | 0.05 | 0.08 |
| 98-594 | 0.16 | 0.76 |
| 98-664 | 0.17 | 0.20 |

TABLE 5

Summary of Tumor Marker Distributions

| Tumor Marker | Threshold | Range |
|---|---|---|
| HER-3 | 0.79 | 0.01~2.80 |
| HER-4 | 0.08 | 0.01~0.89 |
| Heregulin | 0.22 | 0.01~1.08 |
| P-P38-1 | 22.00 | 0~0.05 |

TABLE 6A

Calibration of DU 145 (250,000 receptors per cell)

| Cell Line | Receptors per cell |
|---|---|
| SKBR3 | 60,000 |
| A549 | 85,000 |
| PACA | 150,000 |
| PC3 | 205,000 |
| AU565 | 1,000,000 |
| MDA-MB 468 | 2,000,000 |

TABLE 6B

Quantitation of EGFR by Image Analysis: Tissue

| Tissue | Source | Number of Receptors |
|---|---|---|
| 98-421 | Bladder Cancer | 47K |
| 98-348 | Breast Cancer | 31K |
| 99-1746 | Breast Cancer | 43K |

TABLE 7

HER-2/neu ELISA Quantitation Data and HER-2/neu Image Analysis Quantitation (IA) Data of Four Cell Pellets

| Pellet | ELISA fm/µg | IA fm/µg |
|---|---|---|
| MCF-7 | 0.28 | 0.24 |
| MCF&/HER-2 | 0.53 | 0.55 |
| MDA-MB543 | 1.31 | 1.37 |
| SKBR3 | >3.07 | 3.04 |

TABLE 8A

| Calibrator Cells | | |
|---|---|---|
| Cell Line | Receptors/cell | fm/µg |
| MDA-MB-361 | 92,000 | 0.19 |
| SKBR 3 | 2,400,000 | 3.90 |
| MCF7 | 60,552 | 0.14 |
| AU537 | 2,585,637 | 4.20 |

TABLE 8B

| Tissues | | |
|---|---|---|
| Specimen | Receptors/cell | fm/µg |
| 99-1908 | 611,066 | 1.02 |
| 99-1973 | 1,202,527 | 1.98 |
| 99-1976 | 2,567,438 | 4.20 |

TABLE 9

Prognostic Role of HER-4, Heregulin, and JNK-p38 in Patients with Stage II Breast Cancer Treated with Doxorubicin-Based Adjuvant Chemotherapy

| Tumor Marker | Total | # With Records Available | 5-Yr Disease Free Survival (%) | P |
|---|---|---|---|---|
| HER-4 | 35 | 20 | 57 | |
| <0.08 | 15 | 4 | 80 | <0.01 |
| >0.08 | 20 | 16 | 39 | |
| Heregulin | | | | |
| <0.245 | 18 | 6 | 78 | <0.01 |
| >0.245 | 17 | 14 | 35 | |
| P-p38 | | | | |
| 0 | 24 | 16 | 46 | 0.06 |
| >0 | 11 | 4 | 81 | |

What is claimed is:

1. A method for determining the quantity of a target protein in cells of a biological sample, the method comprising the steps of:

(a) immunohistochemically staining said target protein in a plurality of control cell pellets using a detectably labeled antibody directed against said target protein, wherein the quantity of the target protein in the plurality of control cell pellets is independently known, and wherein the expression level of the target protein in each of the plurality of control cell pellets is not the same, (b) identifying pixels corresponding to cellular area to be determined for each of the stained plurality of control cell pellets in (a);

(c) determining an average optical density of stained target protein per pixel of cellular area identified in (b) for each of the stained plurality of control cell pellets in (a);

(d) generating a calibration curve relating the known quantity of said target protein with said average optical density of stained target protein per pixel of cellular area as determined in (c) for each of the plurality of control cell pellets;

(e) immunohistochemically staining said target protein from said biological sample using said detectably labeled antibody directed against said target protein;

(f) identifying the pixels corresponding to the cellular area to be determined in said biological sample;

(g) determining an average optical density of stained target protein per pixel of cellular area identified in (f) in said biological sample;

(h) determining the quantity of said target protein in said biological sample by comparing the average optical density of stained target protein per pixel of cellular area as determined in step (g) in said biological sample to the calibration curve as generated in step (d), wherein the quantity of said target protein is derived from the calibration curve.

2. The method of claim 1, wherein the target protein is a protein that is expressed in malignant cells in an animal.

3. The method of claim 2, wherein the target protein is Her-2/neu, Her-3, Her-4, estrogen receptor, prostate-specific antigen, Epidermal Growth Factor Receptor ("EGFR"), AKT, p13 kinase or Mitogen-Activated Protein Kinase ("MAP kinase").

4. The method of claim 1, wherein the plurality of control cell pellets are prepared from cultured cell lines.

5. The method of claim 4, wherein the cultured cell lines express a reproducible amount of the target protein.

6. The method of claim 1, wherein the quantity of said target protein from each of the control cell pellets is known by determining the quantity of said target protein using an immunological reagent, wherein said immunological reagent is the same or different than the detectably labeled antibody of step (a).

7. The method of claim 6, wherein the quantity of said target protein from each of the control cell pellets is known by determining the quantity of said target protein by Enzyme Linked Immunosorbent Assay ("ELISA").

8. The method of claim 1, wherein the quantity of said target protein from each of the control cell pellets is normalized to the total amount of protein in the cell pellet.

9. The method of claim 8, wherein the quantity of said target protein from each of the control cell pellets is normalized to the total amount of protein per cell.

10. The method of claim 8, wherein the quantity of said target protein in the calibration curve is expressed as number of target protein molecules per cell.

11. The method of claim 1, wherein the average optical density of stained target protein per pixel of cellular area is determined using image analysis.

12. The method of claim 11, wherein said biological sample is stained with a multiplicity of stains, and wherein the image analysis is performed by splitting a signal comprising an optical density of the stained target protein in said biological sample into a multiplicity of signals that are processed using optical filters having different absorption and transmittance properties, so that each signal is specific for one of said multiplicity of stains used to stain the cells in the biological sample.

13. The method of claim 1, wherein the detectable label is a chromogen or a fluorophore.

14. The method of claim 1, wherein said biological sample is a tissue or cell sample removed from a subject.

15. The method of claim 1, wherein the calibration curve is linear.

16. The method of claim 1, wherein the immunohistochemical staining of (e) is performed with the same reagents as is used for the immunohistochemical staining of (a).

17. The method of claim 1, wherein the cellular area is the nucleus.

18. The method of claim 1, wherein the cellular area is the membrane.

* * * * *